United States Patent
Ng et al.

(10) Patent No.: US 7,718,569 B2
(45) Date of Patent: May 18, 2010

(54) COMPOSITE CATALYST FOR THE SELECTIVE OLIGOMERIZATION OF LOWER ALKENES AND THE PRODUCTION OF HIGH OCTANE PRODUCTS

(75) Inventors: Flora Tak Tak Ng, Waterloo (CA); Garry Llewellyn Rempel, Waterloo (CA); Bongani Nkosi, Vanderbijlpark (ZA)

(73) Assignee: University of Waterloo, Waterloo (CA)

( * ) Notice: Subject to any disclaimer, the term of this patent is extended or adjusted under 35 U.S.C. 154(b) by 602 days.

(21) Appl. No.: 10/582,333

(22) PCT Filed: Dec. 10, 2004

(86) PCT No.: PCT/CA2004/002111

§ 371 (c)(1),
(2), (4) Date: Oct. 23, 2006

(87) PCT Pub. No.: WO2005/056503

PCT Pub. Date: Jun. 23, 2005

(65) Prior Publication Data

US 2007/0123743 A1    May 31, 2007

Related U.S. Application Data

(60) Provisional application No. 60/528,699, filed on Dec. 12, 2003.

(51) Int. Cl.
    B01J 23/00 (2006.01)
(52) U.S. Cl. ..................................... 502/355; 585/277
(58) Field of Classification Search ......... 502/300–355; 585/250–277, 500–532
See application file for complete search history.

(56) References Cited

U.S. PATENT DOCUMENTS

| | | | |
|---|---|---|---|
| 1,400,849 A | 12/1921 | Backhaus | |
| 3,562,351 A * | 2/1971 | Mertzweiller et al. | 585/511 |
| 4,085,068 A * | 4/1978 | Gallagher et al. | 502/254 |
| 4,194,964 A | 3/1980 | Chen et al. | |
| 4,215,011 A | 7/1980 | Smith, Jr. | |
| 4,232,177 A | 11/1980 | Smith, Jr. | |
| 4,250,052 A | 2/1981 | Smith, Jr. | |
| 4,302,356 A | 11/1981 | Smith, Jr. | |
| 4,439,350 A | 3/1984 | Jones, Jr. | |
| 4,443,559 A | 4/1984 | Smith, Jr. | |
| 4,476,341 A | 10/1984 | Mathys et al. | |
| 4,935,577 A | 6/1990 | Huss et al. | |
| 5,003,124 A | 3/1991 | Smith, Jr. et al. | |
| 5,057,468 A | 10/1991 | Adams | |
| 5,118,900 A | 6/1992 | Drake | |
| 5,189,001 A | 2/1993 | Johnson | |
| 5,235,102 A | 8/1993 | Palmer et al. | |
| 5,244,929 A | 9/1993 | Gottlieb et al. | |
| 5,254,783 A | 10/1993 | Saleh et al. | |
| 5,262,012 A | 11/1993 | Smith, Jr. | |
| 5,266,546 A | 11/1993 | Hearn | |
| 5,348,710 A | 9/1994 | Johnson et al. | |
| 5,417,938 A | 5/1995 | Shelden | |
| 5,431,890 A | 7/1995 | Crossland et al. | |
| 5,457,268 A | 10/1995 | Greene et al. | |
| 5,510,555 A | 4/1996 | Brunelli et al. | |
| 5,622,997 A | 4/1997 | Tennison et al. | |
| 5,730,843 A | 3/1998 | Groten et al. | |
| 5,877,363 A | 3/1999 | Gildert et al. | |
| 5,942,456 A | 8/1999 | Crossland et al. | |
| 6,025,533 A | 2/2000 | Vora et al. | |
| 6,117,812 A | 9/2000 | Gao et al. | |
| 6,242,661 B1 | 6/2001 | Podrebarac et al. | |
| 6,274,783 B1 | 8/2001 | Gildert et al. | |
| 6,291,719 B1 * | 9/2001 | Gao et al. | 568/596 |
| 2001/0006154 A1 | 7/2001 | Krug et al. | |

FOREIGN PATENT DOCUMENTS

| | | |
|---|---|---|
| GB | 2 193 907 A | 2/1988 |
| WO | WO 02/092216 | 11/2002 |

OTHER PUBLICATIONS

Beltrame et al, (1994) *Appl. Catal., A: general*, 100, 39-48.
Heveling et al, (2003) "Activity and selectivity of nickel-exchanged silica-alumina catalysts for the oligomerization of propene and 1-butene into distillate-range products"; *Applied Catalysis A: General 248* p. 239-248.
Keim et al, (1979) *Mol. Catal.*, 6, 79.
Kister & Larson (1997)"Packed Distillation Tower Design", *McGraw-Hill*, Section 1.6, p. 314-333.
Marcel Dekker Inc. (ed. A Cybulski & J. Moulijn) (1998) "*Structured Catalysts and Reactors*".
Ralph F. Strigle, Jr. (1987) "Random Packings and Packed Towers Design and Applications", *Gulf Publishing Company*, Houston Texas. p. 1-10.

\* cited by examiner

*Primary Examiner*—Edward M Johnson
(74) *Attorney, Agent, or Firm*—Marshall, Gerstein & Borun LLP

(57) ABSTRACT

The present invention relates to a) a catalytic composite comprising a support structure and a catalytic species that is deposited on the support structure, b) a process for the selective oligomerization of lower alkenes and mixtures of alkenes, which process comprises contacting the lower alkenes with the catalytic composite in a catalytic distillation apparatus and under catalytic distillation conditions, and c) a process for producing high octane products, which process comprises hydrogenating one or more catalytic distillation apparatus and under catalytic distillation conditions.

47 Claims, No Drawings

US 7,718,569 B2

COMPOSITE CATALYST FOR THE SELECTIVE OLIGOMERIZATION OF LOWER ALKENES AND THE PRODUCTION OF HIGH OCTANE PRODUCTS

CROSS REFERENCE TO RELATED APPLICATIONS

This application is a national phase application based on international application no. PCT/CA2004/002111, filed Dec. 10, 2004, which claims the benefit of U.S. Provisional Application No. 60/528,699, filed Dec. 12, 2003, the content of which is incorporated herein by reference.

FIELD OF THE INVENTION

This invention relates to the oligomerization of lower alkenes and mixtures of alkenes by catalytic distillation. More specifically, the invention relates to a catalytic composite as a catalyst and packing media in a catalytic distillation column for the selective oligomerization of lower alkenes. In addition, the invention also relates to the hydrogenation of alkenes or of the products from the selective oligomerization to produce high octane products.

BACKGROUND OF THE INVENTION

Catalytic distillation (CD) combines catalytic reaction and separation in a single distillation unit. This idea was first implemented early in the 1920s for the production of esters (Backhaus, 1921) and has been applied to a number of chemical processes based on homogeneous catalysts. The advantages of combining reaction and separation were not fully appreciated until 1980, when Smith patented a new catalytic distillation technology using heterogeneous catalysts (Smith, 1980).

Conventional chemical processes that utilise a distillation process (non-catalytic) mainly consist of two separate unit operations. These include a unit hosting chemical reactions and another unit for separating the different components from the resulting reaction mixture. Under such circumstances, it is difficult to recycle the heat produced by the chemical reaction, and cooling is often needed to control the temperature in the reaction zone, thus resulting in ineffective energy utilization in the process. In addition, the productivity of a preferred compound is often limited by the conversion and selectivity in a chemical process due to equilibrium limitations. Since heat and mass transfer resistance are common problems in such a reaction unit, poor catalytic performance may occur together with a shorter catalyst lifetime.

In order to avoid the chemical equilibrium limitation and make full use of reaction heat, the simple combination of a chemical reaction unit with the separation unit in a traditional distillation column has provided a successful approach for a number of catalytic reaction processes. This combination was first utilized for homogeneous reaction systems. Because these systems involve both reaction and distillation, the name reactive distillation (RD) was coined for these processes. The traditional RD processes were mainly based on homogeneous reaction systems; thus, RD is also referred to as homogeneous catalytic distillation. Although RD processes often result in both high reaction rates and high selectivity to certain desired products, several disadvantages still prevail. These include separation of catalyst from the reaction products, recovery of catalyst, column fouling and corrosion. In addition, if the product purity with respect to the catalyst composition is strictly necessary, the products have to be intensively treated after reactive distillation to ensure a satisfactory level of catalyst removal, which can increase operating costs.

For gas and/or liquid reactions occurring on the surface of solid catalysts (heterogeneous systems), reaction products can be easily separated from the catalyst system. If a heterogeneous reaction can be managed within a distillation unit, the difficulty of separation encountered in homogeneous catalytic distillation can be overcome. However, another factor that must be addressed is to ensure that sufficient catalyst is placed into the column without significantly increasing the pressure drop. It was not until 1980 that Smith (1980) patented a method of suspending catalyst pellets inside a distillation column using fibreglass containment bags, which are known as Texas teabags. Use of these bags permits the use of heterogeneous catalysts without giving rise to large increases in pressure drop. In contrast to homogeneous catalytic distillation, heterogeneous catalytic distillation is preferentially termed catalytic distillation (CD).

In the CD process, the solid catalyst has to be packed in a suitable manner inside the distillation column so as to maximize contact between vapour and liquid phases, but to minimize column flooding. Indeed, various methods have been reported for supporting or containing catalysts [Crossland et al., U.S. Pat. No. 5,431,890; Hearn, U.S. Pat. No. 5,266,546; Shelden, U.S. Pat. No. 5,417,938]. It should be noted that with all these methods, the catalyst is enclosed inside a device which can increase the mass transfer resistance of the liquid and gas phases in the column.

Since a catalytic distillation process combines heterogeneous reaction and separation in a single distillation column, the following advantages can often be obtained over conventional fixed bed reactors:

i) The capital and production costs are reduced because two operations are combined in a single unit.

ii) The energy consumption can be minimized as the heat of the reaction is used for the in-situ vaporization of the reactants.

iii) The conversion of the reactant can be enhanced through internal recycling.

iv) As the reaction products are continuously removed from the reaction site or the surface of catalyst as they are formed, the normal chemical equilibrium limitation does not apply, thus allowing a higher conversion to be achieved.

v) The selectivity for a desired product can also be improved by continuously removing of the product away from the reaction site or the catalyst surface as the product is formed.

vi) The heat generated by the reaction can be efficiently carried away by the liquid and vapour, thus eliminating or avoiding the formation of hot spots on or in the vicinity of the catalytic site. This movement of the flushing liquid or vapour has a flushing effect in that it removes the higher molecular weight oligomerization products down from the reaction zone, and thereby freeing the catalytic site for another reaction. The possible fouling and poisoning of the catalyst are greatly reduced.

vi) The catalyst lifetime can also be improved because the catalyst bed is surrounded by hot or boiling liquid and vapour that constantly exert a flushing on the catalyst site. Such a flushing effect remove products and by products that can undergo further reaction which can lead to possible fouling and poising of the catalyst.

Although there are many advantages for CD technology over the conventional processes mentioned above, catalytic distillation is not suitable for use in all chemical reaction process. In order to achieve the benefits from a CD process, a chemical reaction system should preferably satisfy the following requirements:

i) The reaction should take place in the liquid phase.

ii) The catalyst should be heterogeneous and stable thermally as well as chemically and physically to retain its structural integrity for maintenance of a long lifetime.

iii) The reaction should be exothermic and in situations where the reaction is equilibrium limited, the CD process presented the option to shift that equilibrium more to the right to achieve higher conversion and higher productivity much more efficiently.

One chemical reaction that satisfies these requirements is the oligomerization of lower alkenes (alkene molecules having from 2 to 6 carbon atoms). Alkylation and oligomerization of lower alkenes was first disclosed by Huss and Kennedy (1990) and Smith et al. (1991). The oligomerization of lower alkenes is an important industrial reaction and represents a route to the production of intermediates used for the production of motor fuels, plasticizers, pharmaceuticals, dyes, resins, detergents, lubricants and additives (O'Connor and Kojima, 1990). With respect to butene oligomerization, the less branched dimer products, octenes, are particularly useful in the manufacture of plasticizers. If heavily branched, the mixture can be used as a gasoline blender.

Historically, the exploitation of all of the $C_4$ fractions obtained as by-product from hydrocarbon fluid catalytic cracking and steam cracking to produce high value products (high octane value product) has been lacking. Butadiene, a component of the by-product is useful for rubber production and is extracted from the by-product, leaving the remaining $C_4$ fractions as a mixture referred to as Raffinate I. The isobutene that is contained in Raffinate I was used as a source for production of methyl tert-butyl ether (MTBE). The remaining components of the $C_4$ fractions after the removal of isobutene, consisting mainly of linear $C_4$ hydrocarbon (butenes), was mainly used as a gasoline blender, albeit a poor one. In certain cases, this product was simply disposed of by flaring. In Raffinate II, n-butene is present at an average content from 70% to 80% and in some cases can be in the ninety percentage ranges. Using this resource, smaller oligomers, particularly $C_8$ and $C_{12}$, are being produced by current catalytic oligomerization processes.

A variety of butene oligomerization processes have been proposed (Keim et al., 1979; Mathys, 1984; Beltrame et al., 1994) based on homogeneous and heterogeneous reactions. These processes are exclusively focused on the catalyst selection and process optimization so that a high oligomerization rate with a high selectivity to desired products, mainly short and less branched oligomers, can be obtained.

The use of catalytic distillation to enhance the oligomerization of alkenes was first disclosed in U.S. Pat. No. 5,003,124 to Smith in 1991. This process utilized an acidic ion exchange resin placed inside a fibre glass bag.

Further research has been carried out in the field of alkene oligomerization, but in most cases, the oligomerization catalyst is contained within a second structure such as a cloth or mesh bag, and the reactants have to pass through this structure to access the catalyst. Likewise, the products have to pass through the structure to be removed away from the catalyst. In one such example, Podrebarac (1992) studied butene dimerization in a CD column using a nickel exchanged zeolite catalyst, where the zeolite was placed directly in fibreglass bags. The zeolite catalyst in this case was quickly deactivated by the production of undesirable long chain oligomers, which oligomers blocked the active sites on the catalyst. The system also displayed poor selectivity to octane due to the mass transfer resistance caused by the fibreglass bags.

Additional work has been carried out to find alternative methods of placing the catalyst directly in the reactive zone of the distillation column, without resorting to the containment of the catalyst in secondary structures such as cloth or mesh bags.

U.S. Pat. No. 6,291,719 B1 to Gao et al. discloses dual-functional catalyst structures having very specific shapes. These catalyst structures, which are formed from a resin catalyst, a metal oxide superacid catalyst or a molecular sieve catalyst, are shown to be suitable for etherification reactions, alkylation reactions, hydrogenation reactions and for the decomposition of MTBE. U.S. Pat. No. 6,291,719 B1 discloses catalyst structures which are limited to two very specific shapes, and the materials used also possess markedly low surface area values.

U.S. Pat. No. 5,244,929 to Gottlieb et al. also discloses moulded organic catalyst bodies made of strongly acid or basic ion exchange resins.

SUMMARY OF THE INVENTION

In one aspect, the present invention provides a catalytic composite for use in a catalytic distillation apparatus, the catalytic composite comprising:

a) a support structure, made of an inorganic oxide, having a void fraction ranging from 0.30 to 0.95, a surface area of from 40 $m^2/g$ to 500 $m^2/g$, and a crush strength of from 2.4 to 9.9 kg per structure unit, the support structure having a shape selected from a ring, a hollow cylinder, a cross or multi partition ring or cylinder with 2, 3, or 4 cell partitions, a saddle, a solid ring, a solid cylinder, a sphere, and a honeycomb body; and b) from 0.01 to 10% by weight of a catalytically active species, based on the weight of the catalyst, which is deposited on the support structure.

In another aspect, the present invention provides a catalytic composite for use as a hydrogenation catalyst in a catalytic distillation apparatus, the catalytic composite comprising:

a) a support structure, made of an inorganic oxide, having a void fraction ranging from 0.30 to 0.95 and a crush strength of from 2.4 to 9.9 kg per structure unit, the support structure having a shape selected from a ring, a hollow cylinder, a cross or multi partition ring or cylinder with 2, 3, or 4 cell partitions, a saddle, a solid ring, a solid cylinder, a sphere, and a honeycomb body; and b) from 0.01 to 10% by weight of palladium, platinum or rhodium, based on the weight of the catalytic composite, which is deposited on the support structure.

In still another aspect, the present invention provides a process for the selective oligomerization of a lower alkene to a $C_6$-$C_{18}$ alkene, which process comprises contacting the lower alkene with a catalytic composite as described herein, under catalytic distillation conditions.

In still another aspect, the present invention provides a process for the hydrogenation of an alkene to an alkane, which process comprises contacting the alkene with a catalytic composite as described herein, and hydrogen, under catalytic distillation conditions.

In still another aspect, the present invention provides a process for preparing high octane compounds, the process comprising:

a) contacting a $C_2$ to $C_6$ alkene with a catalytic composite as described herein, under catalytic distillation conditions, to obtain a $C_6$ to $C_{18}$ alkene; and b) contacting the $C_6$ to $C_{18}$ alkene from step a) with a catalytic composite as described herein which is suitable for hydrogenation, and hydrogen, under catalytic distillation conditions, to obtain a $C_6$ to $C_{18}$ alkane.

In still another aspect, the present invention provides a process for preparing high octane compounds, the process comprising:

a) contacting isobutene with a catalytic composite as described herein, under catalytic distillation conditions, to obtain trimethylpentene; and b) contacting trimethylpentene with a hydrogenation catalyst, and hydrogen, under batch reaction conditions or under hydrogenation reaction conditions to obtain trimethylpentane.

In still another aspect, the present invention provides a process for the production of $C_6$-$C_{18}$ alkenes, which process comprises contacting a mixture of $C_2$-$C_6$ alkenes with a catalytic composite as described herein, under catalytic distillation conditions.

In still another aspect, the present invention provides a process for the selective oligomerization of a lower alkene to a $C_6$-$C_{18}$ alkene, which process comprises contacting a mixture of $C_2$ to $C_6$ alkenes and $C_1$ to $C_6$ alkanes with a catalytic composite as described herein, under catalytic distillation conditions.

In still another aspect, the present invention provides a process for the hydrogenation of butadiene, the process comprising contacting butadiene with a catalytic composite composite as described herein which is suitable for hydrogenation, and hydrogen, under catalytic distillation conditions.

In still another aspect, the present invention provides a process for the selective hydrogenation of methylacetylene and propadiene in a C3 fraction to provide propylene, the process comprising contacting the C3 fraction with a catalytic composite composite as described herein which is suitable for hydrogenation, and hydrogen, under catalytic distillation conditions.

In still another aspect, the present invention provides a process for the selective hydrogenation of allene and propyne in a fluid catalytic cracking (FCC) stream, the process comprising contacting the FCC stream with a catalytic composite composite as described herein which is suitable for hydrogenation, and hydrogen, under catalytic distillation conditions.

In still another aspect, the present invention provides a process for the selective hydrogenation of butadiene in a raffinate I or a raffinate II stream to provide a butene, the process comprising contacting the raffinate I or the raffinate II stream with a catalytic composite composite as described herein which is suitable for hydrogenation, and hydrogen, under catalytic distillation conditions.

Specific embodiments of the present invention will be better understood when consideration is given to the following description, including the examples and tables of data presented therein.

DESCRIPTION OF THE EMBODIMENTS

Base Materials for the Support Structure

The catalyst support material (support structure) can be selected, for example, from inorganic oxides. Examples of suitable inorganic oxides include alumina, zirconia, silica, titania and any chemical and physical combinations thereof, such as silica/alumina. Mixtures of structurally designed materials such as molecular sieves and zeolites with selected inorganic oxides are also suitable combinations for use as catalyst supports. Of these, alumina is preferred, and γ-alumina is more preferred. The inorganic oxides, including the structurally designed materials, are commercially available as powdered materials which serve as the base material for support structures.

Support Structures

The powdered base materials can be shaped, moulded or otherwise formed into specific structures (herein referred to as support structures) without compromising the integrity of the materials (e.g. without altering the crystalline state or the elemental composition and physical properties of the materials). The support structure preferably takes a specific shape or form, which shape or form is selected from the various shapes such as rings or cylinders, cross or multi partition rings or cylinders with 2 cell, 3 cell and 4 cell partitions, saddles (such as Intalox or Beryl saddles), solid rings or cylinders, spheres, and honey comb bodies (single or double).

The size of the support structure can vary, and different sizes can be used for columns having different dimensions. For example, the cylindrical support structures can be as large as 5 cm in diameter and as small as 6 mm. The preferred ratio of length to diameter for these cylinders is 1:1, but this ratio can vary from 1:3 to 3:1.

In addition to the shape or form, the surface area of the catalytic support is important and is a factor taken into consideration when the catalytic support is selected for the formation of the support structure. A catalyst support with a large surface area is highly desirable. The BET surface area of the support structure can be selected from within the range of from 40 to 600 $m^2/g$ depending on the process, the feed and the reaction. Preferably, the surface area ranges from 60 to 450 $m^2/g$, and most preferably, from 80 to 350 $m^2/g$.

The support structure should be robust or strong. The crush strength of a support structure provides a relative measure of its strength and its ability to withstand attrition when subjected to varying pressures and temperatures. The support structure preferably has a rush strength of from 2.4 kg to 9.9 kg per unit (i.e. per single structure) or per unit of the catalytic composite. The catalytic composite is obtained from the support structure after the deposition of a catalytically active species, such as a metal compound or an acidic salt, on its surface.

The column void volume fraction is a feature that directly relates to the support structure when such structure is randomly packed in a reaction column (e.g. catalytic distillation column). The shape or form of the support structure determines the column void volume fraction, which represents the fraction of space in the column not occupied by the solid portion of the support structure. The shape or form of support structure influences the void volume in two ways. Firstly, the space formed or enclosed within a hollow (volume enclosed wholly or partially) of the support structure. Secondly, the space generated by the non-uniform orientation (relative angles assumed) of the support structure and interaction among the individual support structure when randomly loaded in the reactor column. The non-uniform orientation of the support structures does not significantly hinder the overall flow of the liquid or vapour within the column, which is for practical purposes unidirectional, but it does provide a random distribution as gases or liquid flow through the packed structures. Such a flow pattern enhances gas or liquid contact with the support structures, which permits a better conversion of vapour to liquid within the void spaces in the column and also lowers the mass transfer resistance through the reactive zone of the distillation column.

A void fraction of 1.0 represents a completely empty column, while void fractions of 0.30 and 0.95 represent 30 and 95 percent of empty space in the column, respectively. The void fraction within the column which holds the catalytic composite or a combined mixture of catalytic composite plus inert support structures can range from 0.30 to 0.95. Preferably, the void fraction is from 0.40 to 0.85, and more preferably the void fraction is from 0.55 to 0.70. For example, a catalytic composite in the form of a cylinder having a 6 mm length and 6 mm outer diameter gives a column void fraction of 0.50.

The haphazard flow pattern caused by the structures, the dilution of the amount of catalyst in the column, and the simultaneous fractionation and separation of the product collectively contribute to the selectivity of the reaction carried out in a catalytic distillation column loaded with the catalytic composite described herein. These features can therefore be seen or defined as properties of the catalytic composite or properties a homogenous mixture of the catalytic composite and the catalyst support structures when randomly packed in a column. Alternatively, these features can be termed as the random packing characteristics of the catalytic composite.

The surface features of the support structures affect the amount of catalyst that can be loaded on such structures. Surfaces that are rendered smooth or non porous or glazed by the shaping process or otherwise, are undesirable for depositing a wide percentage variation of catalyst loadings. Only traces of catalyst (less than 0.01%) were found on smooth or low porosity structures. This is most likely due to the fact that the sites that accommodate the catalyst are blocked by the shaping process. A certain level of surface unevenness or roughness aids in the loading of the catalyst. A range of possible pore sizes is desirable to permit a wide range of catalyst loadings. BET adsorption studies of support structures and catalytic composites derived from alumina rings used herein showed both mesopores and micropores. Pore diameters range from 70 angstrom to less than 20 angstrom. The adsorption studies indicated that the catalysts are mostly to be found in the mesopores of the structure.

The Catalytic Composite

The catalytic composite is comprised principally of two separate components, namely a support structure and an active metal or metal ion species as catalyst. These are combined or synthesised by a procedure to produce a composite material without the loss of features and properties comprising of both components to constitute or form the catalytic composite.

Various catalytically active species can be deposited on the support structures described above to give the catalytic composite. Examples of active species include metals and metal ions from Groups VI, VII and VIII. These metals or metal ions can be loaded from corresponding metal salts or metal complexes. Of these metals and metal ions, nickel ions loaded from nickel salts, which are especially effective for the oligomerization of lower alkenes, are preferred as the active species for oligomerization. More preferably, the nickel ions loaded from aqueous solutions of nickel sulphate, or aqueous solutions of nickel chloride and ammonium sulphate are used as the active catalytic species. Metals used as the catalytic species for oligomerization are also preferably in the +1 or +2 oxidation state. As the oligomerization is acid catalysed, acid and acidic salts can be deposited on the support and used as catalyst. In addition, the oligomerization catalysts comprising nickel ions can be further enhanced through exposure to solutions of sulphate salts such as ammonium sulphate, phosphate salts such as ammonium phosphate and acids such as sulphuric acid, phosphoric acid or toluenesulfuric acid. Such solutions are herein referred to as catalyst enhancers.

The catalytically active species are not necessarily metallic, as certain salts, such as ammonium sulphate, can be used. For example, ammonium sulphate is a suitable catalytically active species for the dimerization of isobutene in the presence of hydrogen.

Metal loaded from metal complexes of palladium, platinum, rhodium and nickel are effective for hydrogenation of alkenes, including hydrogenation of octenes and methyl substituted pentenes produced by the oligomerization of butenes by the nickel catalyst described herein. Metal salts can also be used as catalytic species in the hydrogenation process if the metal ions derived from the salts can be reduced to give metal species that are active.

The amount of catalyst species on the support structure is dependent on the concentration of metal salt or the metal complex in solution, and to a lesser extent on the length of the exposure period of the support structure to the solution. The amount of catalytic species can be from 0.01 to 10% by weight, for example of from 0.05 to 10% or from 0.1 to 8% by weight.

A catalytic composite for use as an oligomerization catalyst can, for example, contain nickel in an amount of from 0.1 to 8% by weight, relative to the weight of the composite. Preferably, the amount of nickel is from 0.2 to 6.0% by weight, and more preferably, from 0.5% to 5% by weight.

A catalytic composite for use as a hydrogenation catalyst can, for example, contain palladium in an amount of from 0.05 to 8% by weight, relative to the weight of the composite. Preferably, the amount of palladium can be, for example, from 0.1 to 8%, from 0.2 to 6%, from 0.2 to 5%, from 0.5 to 5% or from 0.3 to 2% by weight.

Deposition of the metal ions on the support structure can be effected by methods known in the art. Examples of such methods include wet and dry impregnation methods, vaporization methods, absorption techniques, ion-exchange techniques, sol-gel techniques and vapour deposition techniques. A description of such techniques is given in examples 1a and 1b.

Catalytic Distillation Packing

The catalytic composite is effective as a material or a media for the application as catalytic distillation packing when used in a catalytic distillation column because of the large surface area of the composite and the void space obtained when the composite is randomly packed in the column. The catalyst component of the catalytic composite carries out the desired chemical reaction or reactions while the surface area and the void volume is effective for fractionation and separation of the reaction products. The composite can therefore act as a catalyst as well as a fractionation medium. Depending on the type of reaction, the activity of the catalyst, or the level of separation that is desirable, the catalytic composite can be mixed with inert support structures (i.e. support structures that do not contain a catalyst and are inert to reaction) and be used in the catalytic distillation column as catalytic distillation packing. The combination of catalytic composite with support structures as catalytic distillation packing material in a catalytic distillation column can result in an increase in the selectivity of the catalytic distillation process. This increase in selectivity is due to: i) an increase in the void space in the distillation column, and ii) better control on the rate of conversion within the distillation column. For example, in the present invention the composite catalyst made from Raschig rings of 6 mm can be combined with Intalox saddles (inert support structure) in a 1:1 ratio to form a mixture and used as the catalytic distillation packing. Such a randomly packed mixture in the column gives a void volume fraction of 0.55 which is intermediate between that of the rings (0.49) and the saddles (0.62). The presence of such support structures as inert packing materials in the reactive zone can also lead to a better control of the rate of conversion within the distillation column. For exothermic catalytic reactions, there is the possibility that the temperature will increase uncontrollably as the heat produced by the reaction increases the rate of reaction in an exponential manner. This is commonly referred to in the industry as "temperature runaway". Temperature runaway is especially detrimental to the selectivity of certain reactions, such as oligomerization reactions, as higher temperatures result in the formation of unwanted products, such as the formation of polymers instead of oligomers such as dimers. Using support structures as inert packing material within the reactive zone can therefore be beneficial, as they can be used to control or lower the overall rate of conversion in the distillation column by finely dispersing the catalytic composite within the reactive zone. The inert support structures act as a dilution medium for the catalytic composite and at the same time provide additional surface for fractionation to occur. The ratio of such inert packing material to catalytic composite can vary for different catalytic active species. The ratio of inert packing material to catalytic composite can range, for example, from 10:1 to 1:10.

The support structure to be used as inert packing material can be selected from any known packing material that is suitable for use in catalytic distillation. This packing material can have various shapes, such as Raschig rings, Pall rings, penta rings, wagon wheels, honeycomb rings, berl saddles, Intalox saddles, Super Intalox saddles, Hy-Pak packing, Tellerette packing, Maspac packing, Cascade mini-rings, and Nutter rings. The size of the random-packing material used is dependent on the size of the diameter of the distillation column, and it is usually similar in size to the catalytic composite. The inert packing material can be made out of materials similar to those used for the support structure, such as alumina, zirconia, silica, and titania, but it can also be formed out of less porous materials such as silicon carbide, metals, ceramic, and plastics.

Reactants and Products

In the description, the expression "lower alkenes" refers to alkene molecules that have 2 to 6 carbon atoms. Of primary interest are those alkenes that have 4 carbon atoms (1-butene, 2-butene, and isobutene).

The products of the selective oligomerization process of the present invention are principally the dimers and trimers of the $C_2$ to $C_6$ alkenes. These products include alkenes having from 6 to 18 carbon atoms, although the products of most interest are the dimers of the $C_4$ alkenes. These have the general formula $C_8H_{16}$, and they are widely used in the petroleum industry as gasoline additives. The possible dimers of $C_4$ include trimethylpentenes, n-octenes, dimethylhexenes and methylheptenes, of which dimethylhexenes and trimethylpentenes are of greater interest, since the more branched octenes have a higher octane number. In particular, hydrogenation of 2,4,4-trimethylpentene-1 and 2,4,4-trimethylpentene-2 can produce 2,2,4 trimethylpentane which has an octane number of 100. Surprisingly, the octene product obtained from the dimerization of 1-butene produced through the catalytic distillation process of the invention is enriched in dimethyhexenes compared to the octene product obtained from the batch and flow reactors. As dimethylhexenes have a higher octane number than methylheptenes, dimerization of 1-butene in a catalytic distillation column provides added benefit in the form of a higher value octane product from the dimerization of 1-butene.

Process Setup and Optimization

The process of the invention is termed "selective", as the catalytic distillation process using the composite catalyst, or the composite catalyst in admixture with inert support structures, permit a reaction that is selective in generating and removing octenes from the reaction stream. In conventional oligomerization reactions, many products are formed and the resulting mixture of products has to be purified to isolate the desired product. The production of the mixture also limits the overall selectivity of the reaction. With catalytic distillation however, the process variables can be selected so as to enhance the production of predominately a single product or group of products. The process variables can also be selected to control the reaction and to prevent intermediate products that would have normally continued to react under conventional reaction conditions.

Many process variables can be changed when carrying out a CD process, and most of the variables can be optimized for specific reactions or products. Such variables include the position of the feeding inlet, the position of the reactive zone, the operating pressure, and the feed rate.

Position of Feed Inlet

The position of the feed inlet is important as it determines where in the reactor CD column the lower alkene feed stock is introduced and where the reaction commences within the CD column. For the dimerization of 1-butene, it is preferable to have the inlet for the introduction of the 1-butene in the CD located below the catalyst zone or the reactive zone of the column in order to obtain higher selectivity and productivity as compared to when the inlet was located above the catalyst zone or reactive zone (see data in Table 8).

The reaction following introduction of the feed stock above or below the catalyst zone produces a different temperature profile along the catalyst zone and this in-turn affects the conversion and selectivity. The situation is same for isobutene and shown in example 7.

The position of the reactive zone, and therefore of the catalytic composite, in the column can also be varied to optimize the reaction. For the selective dimerization of butene, it is preferred to keep the reactive zone fairly high in the column, as the lower sections usually have a high liquid phase temperature. This high temperature can result in a faster reaction, which favors the formation of large oligomers instead of dimers.

The Effect of Operating Pressure

The operating pressure within the column can also be varied to optimize the CD process. Variation of pressure in the column will change the temperature, and the pressure is therefore chosen such that the temperature in the reaction zone is suitable for the chemical reaction to occur and such that a liquid phase is maintained in the reaction zone. For the dimerization of butene, the operating pressure can be, for example, from 90 to 115 psi, with higher pressures increasing the butene conversion. However, care must be taken as increasing the pressure beyond a certain level can compromise octene selectivity.

The Effect of Feed Rate

The feed rate of the reactant can also be varied to optimize the reaction. High feed rates lead to higher production rates, but they can also have a negative impact on the selectivity of a reaction. In the oligomerization of $C_4$, the selectivity of the $C_8$ product decreases as the feed rate increases because the reaction has a greater tendency to proceed to products of higher molecular weight such as $C_{12}$. In the present invention, the feedstock is preferably mixed with an inert solvent before being fed into the reactor. The presence of the inert solvent reduces the concentration of the reactant in the column, thus permitting a higher selectivity in the reaction. Suitable solvents that can be used include $C_4$ to $C_8$ alkanes, higher alkanes, cycloalkanes and alkyl substituted cycloalkanes Preferably, isopentane is used as the inert solvent. In addition, the inert solvent uniformly dissipates the heat generated by the reaction and it assists in the extraction and removal of any higher oligomers or coke precursors that could deactivate the catalyst. As long as the mass transfer resistance is kept fairly low, which can be achieved by using the catalytic composite of the invention, the separation of the product produced by the distillation column provides good selectivity, even under higher feed rates.

Multiple Catalysts or Reactive Zones

The catalytic distillation column can also be fitted with more than one catalyst or more than one composite catalyst within the same reactive zone, to carry out more than one reaction simultaneously. Alternately, the column can be set up to have two reactive zones, where each zone may contain a different catalyst or a different catalytic composite, where each zone will be subjected to a different temperature profile within the column. These reactive zones filled with different catalysts or different catalytic composites and operating at different temperatures within a single column can therefore carry out more than one reaction, and as a result the column is being made to carry out more than one process. This can be used, for example, when dimerization and hydrogenation is required e.g. dimerization of butene and hydrogenation of the octene produced. In such a case, one of the reactive zones may comprise a composite catalyst such as that given in example 1a for oligomerization and the other reactive zone can comprise a composite catalyst with a hydrogenation catalyst species such as platinum or palladium. Multiple catalysts and catalytic composites in one or more reactive zones can be used for the concurrent or consecutive dimerization of a mixture of different alkenes such as those derived from steam cracking, thermal and catalytic cracking of hydrocarbons. Examples of such mixtures include raffinate streams from steam cracking of naphtha and the light gases obtained from the fluid catalytic cracking (FCC) processes. Raffinate streams usually comprise isobutene, 1-butene, 2-butene, butadiene and butanes. A further raffinate stream, termed Raffinate II, comprises primarily n-butenes, butanes and trace amounts of butadiene. FCC gases comprise a mixture of C3, C4 and C5 alkenes or alkanes, in some instances, they can also comprise C4 or C5 dienes.

Multiple catalytic distillation columns can also be combined to carry out parallel, concurrent or consecutive reaction processes. This can be used, for example, for the concurrent or consecutive dimerization of a mixture of two or more of 1-butene, 2-butene and isobutene. This process can be carried out in 2 or more separate columns using the same of different catalysts or catalytic composites at the same or at different catalyst loadings. Isobutene is more reactive and dimerizes at a much lower temperature than 1-butene, which in turn is more reactive than 2-butene. The first reactive zone can be located at a lower temperature zone of the column to dimerize the isobutene, and the overhead products containing mostly the remaining 1-butene and 2-butene can then be fed to the second or third column which contains a catalyst or catalytic composite in a reactive zone of sufficient temperature to carry out the dimerization of 1-butene and 2-butene. The use of two or more columns provides the flexibility to place the catalytic composites at different height or sections of the distillation column to provide reactive zones with different temperatures and to avoid the further undesirable oligomerization reaction. A combination of multiple columns can also be used to carry out different reactions in a sequential manner such as the dimerization of isobutene and the hydrogenation reactions described above for the production of isooctane (for example 2,4,4-trimethylpentane)

Single or multiple catalytic distillation columns can also be used in conjunction with guard beds. The guard beds are useful to separate unwanted reactants from the reactant streams before such streams are introduced to the CD column. For example, such an operation with a guard bed is useful for a feed stream consisting of butene and butadiene where the dimerization of a butene is required. In such case, butadiene needs to be removed from the feed stream before introduction into the distillation column since it is known that butadiene can poison dimerization catalysts. A guard bed that removes the butadiene by selective adsorption, or that selectively hydrogenates the butadiene to butene can thus be used to pre-treat the feed stream before it is fed into the CD column.

EXAMPLES

The following examples are offered by way of illustration and not by way of limitation.

Example 1a

Preparation of a Catalytic Composite from a Metal Salt

A typical catalytic composite was prepared by the wet impregnation of nickel sulphate onto a support structure derived from γ-alumina rings having a length and a diameter of 6 mm. 13.5 g of nickel sulphate hexahydrate was dissolved in 70 ml of deionized water. This solution was then transferred to a container (beaker) containing 100 g of the support structure (γ-alumina rings). The container was gently tumbled for about 3 mins to achieve a uniform contact between the solution and the rings. After an additional 30 mins of equilibration on the bench, the rings was allowed to dry in air. This was followed by drying at 110° C. for 12 hrs. The dried material was then calcined. The rings was placed in a furnace preset at 110° C. The temperature was then ramped at a rate of 5° C./min to a final temperature of 500° C. Calcination was at 500° C. for 12 hrs after which time the temperature was gradually lowered to room temperature. The catalytic composite so obtained was removed and stored in vials for use. The impregnation procedure was repeated to obtain catalytic composites with an average nickel content of 3% by weight.

Example 1b

Preparation of a Catalytic Composite from a Metal Complexes

The Pd catalytic composite was prepared by a wet-impregnation technique, in which 0.34 g of Pd(acetate)$_2$ was dissolved in a mixture of 50 mL of acetone and 50 mL of water. This solution was added to 16 g of γ-alumina rings (having a surface area of 204 m$^2$/g) which were dried at 200° C. The solution containing the γ-alumina rings was put into a rotary evaporator and the solution was evaporated under reduced pressure. The γ-alumina rings containing Pd were dried in an oven at 90° C. for 1 day, followed by calcination in air at 350° C. for 3 hours and reduction in hydrogen at 350° C. for 3 hours. The catalytic composite containing Pd was protected from air. The weight of Pd in the catalytic composite was 0.7 wt %.

Example 2

Column Operational Set Up and Optimization

The catalytic distillation processes of the examples were carried out on a CD column having a total height of 24 feet, with an inner diameter of 1 inch and a total packing height of 16 feet. The column is principally comprised of a condenser of a total packing height that consists of three segments. An upper non-reactive section, a reaction zone, a lower non-reactive section with a reboiler. The non-reactive sections is filled with catalyst support structure as the inert packing material, such as the ¼" Intalox saddles, or any other known and suitable support structures as mentioned before. The use of Intalox saddles in the non reactive zone produced a void volume fraction of 0.62. The reactive zone consists of the catalytic composite derived from the alumina rings described in example 1 above, the random packing of which produced a void volume fraction of 0.49. Alternatively, the total packing height may consist of a mixture of the catalytic composite and the catalyst support structure. For example the catalytic composite derived from the alumina rings of example 1 and Intalox saddles, a 1:1 mixture of which produced a void volume fraction of such 0.55.

The height of the total packing is dependent on the amount of catalyst on the composite and the feed stock which determines the nature of reaction. The catalytic distillation column normally operates at total reflux. The feed stock, for example 1-butene or isobutene, is mixed with an inert solvent and fed into the column. The inert solvent does not participate in the reaction but is used to dissipate the heat generated by the reaction from the reaction site. The solvent also facilitates the extraction/dissolution and removal of any higher oligomers or coke procurers that could potentially deactivate the catalyst. Depending on the reactants, products and process conditions for a particular operation, solvent can include butanes, pentane, hexanes, higher alkanes and cycloalkanes and alkyl-substituted cycloalkanes. For example, in the dimerization of butenes, isopentane was found to be an effective solvent. Alternatively, the packing material within the column may be continuous, i.e. not segmented into 3 "zones". The packing material in such a case comprises the catalytic composite of the invention alone throughout the column, it comprises a substantially homogeneous mixture of the catalytic composite with an inert packing material.

The following are additional examples of the effect of various process parameters on the oligomerization of butenes.

Example 3

Effect of Reboiler Duty on the Oligomerization of Butenes

The effect of reboiler duty on the CD process for the dimerization and oligomerization of 1-butene was investigated by varying reboiler duty from 200 W to 300 W with a 1-butene feed rate of 48.17 g/h, isopentane feed rate of 13.27 g/h, and 79.45 g of a catalytic composite containing 3.0 wt % Ni at a total pressure of 140 psig. The catalytic composite was mixed with an equal volume of ¼ in Intalox saddles. The results obtained are listed in Table 1.

TABLE 1

Reboiler duty effect on 1-butene oligomerization

| | CD6-V | CD6-IV | CD6-I |
|---|---|---|---|
| Reaction conditions: | | | |
| Operating pressure, psig | 140 | 140 | 140 |
| Reaction temperature, ° C. | 93-111 | 96-114 | 97-117 |
| Reboiler duty, W | 200 | 240 | 300 |
| Amount of catalytic composite, g | 79.45 | 79.45 | 79.45 |
| Nickel concentration, wt % | 3.0 | 3.0 | 3.0 |
| Catalyst position, ft | 12.5-14.5 | 12.5-14.5 | 12.5-14.5 |
| Feed rate of 1-butene, g/h | 48.17 | 48.17 | 48.17 |
| Feed rate of isopentane, g/h | 13.27 | 13.27 | 13.27 |
| Feed position | Below | Below | Below |
| Results: | | | |
| Conversion, wt % | 85.83 | 89.80 | 95.92 |
| Selectivity, wt % | 85.25 | 86.96 | 87.06 |
| Productivity, g/g · h | 0.52 | 0.54 | 0.58 |

Selectivity represent the weight fraction of octenes out of total oligomers.
Productivity represents the weight of oligomers produced by unit weight of catalytic composite per hour.

It can be seen that when the reboiler duty increases, the reaction zone temperature increases by a few degrees, correspondingly the conversion increases from over 85% to over 95%. Surprisingly although the conversion increases, the selectivity to the octene dimer also increases. When consecutive reactions such as the oligomerization of butenes described in this invention was carried out in a conventional reactor, normally the selectivity to dimers decreases when the conversion increases. However, the examples showed that when the oligomerization was carried out in a catalytic distillation packing with this catalytic composite with good mass transfer characteristics as described in this invention, the selectivity to the octene dimer unexpectedly also increased with the conversion.

The effect of reboiler duty on the oligomerization of isobutene was also examined by increasing the reboiler duty from 250 W to 380 W with an isobutene feed rate of 58.30 g/h, isopentane feed rate of 63.25 g/h, and 75 g catalytic composite containing 1.5 wt % Ni mixed with an equal volume of ¼ in Intalox saddles at a total pressure of 60 psig. The results are listed in Table 2.

TABLE 2

Reboiler duty effect on isobutene oligomerization

| | S1CD3 | S1CD4 | S1CD5 | S1CD6 |
|---|---|---|---|---|
| Reaction conditions: | | | | |
| Reaction pressure, psig | 60 | 60 | 60 | 60 |
| Reaction temperature, ° C. | 64-88 | 62-88 | 60-87 | 57-86 |
| Reboiler duty, W | 250 | 300 | 350 | 380 |
| Amount of catalytic composite, g | 75 | 75 | 75 | 75 |
| Nickel concentration, wt % | 1.5 | 1.5 | 1.5 | 1.5 |
| Catalyst position, ft | 10.7-12.7 | 10.7-12.7 | 10.7-12.7 | 10.7-12.7 |
| Feed rate of isobutene, g/h | 58.30 | 58.30 | 58.30 | 58.30 |
| Feed rate of isopentane, g/h | 63.25 | 63.25 | 63.25 | 63.25 |
| Feed position | Below | Below | Below | Below |

TABLE 2-continued

Reboiler duty effect on isobutene oligomerization

|  | S1CD3 | S1CD4 | S1CD5 | S1CD6 |
|---|---|---|---|---|
| Results: | | | | |
| Conversion, wt % | 92.14 | 93.45 | 91.64 | 91.35 |
| Selectivity, wt % | 65.14 | 68.82 | 73.94 | 76.20 |
| Productivity, g/g · h | 0.72 | 0.73 | 0.71 | 0.71 |

Selectivity represents the weight fraction of octenes out of total oligomers.
Productivity represents the weight of oligomers produced by unit weight of catalyst per hour.

As the reboiler duty increases, the selectivity to octenes increased from over 65% to about 76% although the conversion remains essentially the same. This behaviour showed that the feed rate is a little low for 75 g of the catalytic composite since essentially all the isobutene is converted. This example displayed that an increased reboiler duty leads to an increase in reflux flow rate and a better selectivity for the octene dimers.

For the oligomerization of 1-butene or isobutene, it is demonstrated that as the reboiler duty increases, the selectivity to octenes increases, which shows that the catalytic composite is effective for both reaction and separation. Since isobutene is more reactive than 1-butene, a lower system pressure which results in lower temperatures in the distillation column, and a lower Ni loading on the catalytic packing are found to be more suitable for the oligomerization of isobutene.

Example 4

Effect of Operating Pressure. Oligomerization of 1-Butene

The effect of operating pressure on the oligomerization of 1-butene was investigated by changing the operating pressure from 90 psig to 140 psig, with a 1-butene feed rate of 48.17 g/h, isopentane feed rate of 13.27 g/h, and 142 g of catalytic composite containing 3.0 wt % Ni and mixed with 1.2 times the volume of ¼" ceramic Intalox saddles. The results obtained for 1-butene oligomerization are listed in Table 3.

TABLE 3

Operating pressure effect on 1-butene oligomerization

|  | CD-7-I | CD-7-III | CD-7-IV |
|---|---|---|---|
| Reaction conditions: | | | |
| Operating pressure, psig | 90 | 115 | 140 |
| Reaction temperature, ° C. | 83-104 | 94-115 | 106-122 |
| Reboiler duty, W | 300 | 300 | 300 |
| Amount of catalytic composite, g | 142 | 142 | 142 |
| Nickel concentration, wt % | 3 | 3 | 3 |
| Catalyst position, ft | 10.5-14.5 | 10.5-14.5 | 10.5-14.5 |
| Feed rate of 1-butene, g/h | 48.17 | 48.17 | 48.17 |
| Feed rate of isopentane, g/h | 13.27 | 13.27 | 13.27 |
| Feed position | Below | Below | Below |

TABLE 3-continued

Operating pressure effect on 1-butene oligomerization

|  | CD-7-I | CD-7-III | CD-7-IV |
|---|---|---|---|
| Results: | | | |
| Conversion, wt % | 90.91 | 95.32 | 95.61 |
| Selectivity, wt % | 88.38 | 87.91 | 86.66 |
| Productivity, g/g · h | 0.31 | 0.32 | 0.32 |

Selectivity represents the weight fraction of octenes out of total oligomers
Productivity represents the weight of oligomers produced by unit weight of catalytic composite per hour On increasing the operating pressure in a catalytic distillation column, the temperature in the reaction zone increased correspondingly. This resulted in an increased conversion of 1-butene from over 90% to about 96%. However, the selectivity to octenes decreased slightly.

Example 5

Effect of Feed Rate. Oligomerization of 1-Butene

The effect of feed rate on the oligomerization of 1-butene was investigated at first by increasing 1-butene feed rate from 35.31 g/h to 66.37 g/h with 79.45 g catalytic composite containing 3.0 wt % Ni at 140 psig total pressure mixed with an equal volume of ¼ in Intalox saddles (Table 4).

TABLE 4

Effect of feed rate for 1-butene oligomerization

|  | CD6-VIII | CD6-I | CD6-VII |
|---|---|---|---|
| Reaction conditions: | | | |
| Operating pressure, psig | 140 | 140 | 140 |
| Reaction temperature, ° C. | 99-118 | 97-117 | 91-107 |
| Reboiler duty, W | 300 | 300 | 300 |
| Amount of catalytic composite, g | 79.45 | 79.45 | 79.45 |
| Nickel concentration, wt % | 3.0 | 3.0 | 3.0 |
| Catalyst position, ft | 12.5-14.5 | 12.5-14.5 | 12.5-14.5 |
| Feed rate of 1-butene, g/h | 35.31 | 48.17 | 66.37 |
| Feed rate of isopentane, g/h | 9.96 | 13.27 | 17.69 |
| Feed position | Below | Below | Below |
| Results: | | | |
| Conversion, wt % | 96.71 | 95.92 | 88.03 |
| Selectivity, wt % | 87.27 | 87.06 | 87.51 |
| Productivity, g/g · h | 0.43 | 0.58 | 0.74 |

Selectivity represents the weight fraction of octenes out of total oligomers.
Productivity represents the weight of oligomers produced by unit weight of catalytic composite per hour.

The effect was further investigated by increasing 1-butene feed rate from 48.17 g/h to 85.63 g/h with 142 g catalytic composite containing 3.0 wt % Ni and 1.2 times the volume of ¼ in Intalox saddles at 140 psig (Table 5).

TABLE 5

Effect of feed rate for 1-butene oligomerization

|  | CD-7-IV | CD7-V | CD7-VI |
|---|---|---|---|
| Reaction conditions: | | | |
| Operating pressure, psig | 140 | 140 | 140 |
| Reaction temperature, ° C. | 106-122 | 101-122 | 96-122 |

TABLE 5-continued

Effect of feed rate for 1-butene oligomerization

|  | CD-7-IV | CD7-V | CD7-VI |
|---|---|---|---|
| Reboiler duty, W | 300 | 300 | 300 |
| Amount of catalytic composite, g | 142 | 142 | 142 |
| Nickel concentration, wt % | 3 | 3 | 3 |
| Location of catalyst, ft | 10.5-14.5 | 10.5-14.5 | 10.5-14.5 |
| Feed rate of 1-butene, g/h | 48.17 | 66.37 | 85.63 |
| Feed rate of isopentane, g/h | 13.27 | 17.69 | 23.23 |
| Feed position | Below | Below | Below |
| Results: |  |  |  |
| Conversion, wt % | 95.61 | 95.40 | 93.39 |
| Selectivity, wt % | 86.66 | 86.53 | 87.76 |
| Productivity, g/g · h | 0.32 | 0.45 | 0.56 |

Selectivity represents the weight fraction of octenes out of total oligomers
Productivity represents the weight of oligomers produced by unit weight of catalytic composite per hour Increasing the feed rate increased the productivity. At the lower feed rate, the productivity is lower, and hence it is advantageous to maximize the productivity per g of catalyst by varying the feed rate. The effect of increasing the isobutene feed rate from 58.30 g/h to 77.38 g/h with 75 g catalytic composite containing 1.5 wt % Ni and an equal volume of ¼ in Intalox saddles at 60 psig on the isobutene oligomerization is shown in Table 6.

TABLE 6

Effect of feed rate for isobutene oligomerization

|  | S1CD4 | S1CD7 |
|---|---|---|
| Reaction conditions: |  |  |
| Operating pressure, psig | 60 | 60 |
| Reaction temperature, ° C. | 62-88 | 48-56 |
| Reboiler duty, W | 300 | 300 |
| Amount of catalytic composite, g | 75 | 75 |
| Nickel concentration, wt % | 1.5 | 1.5 |
| Location of catalyst, ft | 10.7-12.7 | 10.7-12.7 |
| Feed rate of isobutene, g/h | 58.30 | 77.38 |
| Feed rate of isopentane, g/h | 63.25 | 40.25 |
| Feed position | Below | Below |
| Results: |  |  |
| Isobutene conversion, wt % | 93.45 | 90.71 |
| Isooctene selectivity, wt % | 68.82 | 77.94 |
| Productivity, g/g · h | 0.73 | 0.94 |

Selectivity represents the weight fraction of octenes out of total oligomers.
Productivity represents the weight of oligomers produced by unit weight of catalytic composite per hour It can be seen that the productivity also increased as the feed rate was increased indicating that the productivity could be optimized by the changing the feed rate. There is an optimum ratio of catalyst amount and feedrate for maximum productivity in a CD process.

Example 6

Catalyst Stability. Oligomerization 1-Butene

The catalyst stability for the oligomerization of 1-butene could be seen in the data shown in Table 7.

TABLE 7

Catalyst stability for 1-butene oligomerization

|  | CD6-I | CD6-III | CD6-VI | CD6-IX |
|---|---|---|---|---|
| Reaction conditions: |  |  |  |  |
| Time interval, h | 0-41 | 48-58 | 84-92 | 114-122 |
| Operating pressure, psig | 140 | 140 | 140 | 140 |
| Reaction temperature, ° C. | 97-117 | 96-115 | 95-114 | 95-114 |
| Reboiler duty, W | 300 | 300 | 300 | 300 |
| Amount of catalytic composite, g | 79.45 | 79.45 | 79.45 | 79.45 |
| Nickel concentration, wt % | 3.0 | 3.0 | 3.0 | 3.0 |
| Catalyst position, ft | 12.5-14.5 | 12.5-14.5 | 12.5-14.5 | 12.5-14.5 |
| Feed rate of 1-butene, g/h | 48.17 | 48.17 | 48.17 | 48.17 |
| Feed rate of isopentane, g/h | 13.27 | 13.27 | 13.27 | 13.27 |
| Feed position | Below | Below | Below | Below |
| Results: |  |  |  |  |
| Conversion, wt % | 95.92 | 96.12 | 95.63 | 95.30 |
| Selectivity, wt % | 87.06 | 86.48 | 86.49 | 88.29 |
| Productivity, g/g · h | 0.58 | 0.58 | 0.58 | 0.58 |

Selectivity represents the weight fraction of octenes out of total oligomers.
Productivity represents the weight of oligomers produced by unit weight of catalytic composite per hour.

Over a period of 122 hours, at a reboiler duty of 300 W, 1-butene feed rate of 48.17 g/h, isopentane feed rate of 13.27 g/h, and 79.45 g catalytic composite containing 3.0 wt % Ni and an equal volume of ¼ in Intalox saddles at 140 psig, the conversion, selectivity and productivity are essentially the same over the 122 h period. These data showed that the catalytic composite is very stable in the CD process for butene oligomerization. After the reaction was terminated, the catalytic composite was removed from the column. It was observed the catalytic composite remains intact indicating the mechanical strength of the composite is suitable for use in the CD column. Surface area measurement of the catalytic composite before and after the oligomerization were 183.7 $m^2$/g and 182 $m^2$/g respectively, indicating the stability and resistance of the catalytic composite to deactivation.

Example 7

Effect of Feed Position. Oligomerization of 1-Butene and Isobutene

The position of feed inlet to the distillation column, i.e. whether the feed was above or below the catalyst zone, while all the other process conditions such as pressure, catalytic composite, reboiler duty and feedrate are kept the same, could also result in a change in productivity and selectivity. Examples obtained for 1-butene and isobutene are shown in Tables 8 and 9. The results show that variation of feed inlet position will have an effect on productivity and selectivity.

TABLE 8

Feed position effect on 1-butene oligomerization

|  | CD5-I | CD5-II |
|---|---|---|
| Reaction conditions: |  |  |
| Operating pressure, psig | 130 | 130 |
| Reaction temperature, ° C. | 118-125 | 114-119 |

TABLE 8-continued

Feed position effect on 1-butene oligomerization

|  | CD5-I | CD5-II |
|---|---|---|
| Reboiler duty, W | 300 | 300 |
| Amount of catalytic composite, g | 84.64 | 84.64 |
| Nickel concentration, wt % | 3.0 | 3.0 |
| Catalyst position, ft | 10.5-12.5 | 10.5-12.5 |
| Feed rate of 1-butene, g/h | 51.60 | 51.60 |
| Feed rate of isopentane, g/h | 14.26 | 14.26 |
| Feed position | Below | Above |
| Results: | | |
| Conversion, wt % | 94.39 | 86.89 |
| Selectivity, wt % | 70.10 | 65.46 |
| Productivity, g/g · h | 0.58 | 0.53 |
| C8 productivity, g/g · h | 0.41 | 0.35 |

Selectivity represents the weight fraction of octenes out of total oligomers.
Productivity represents the weight of oligomers produced by unit weight of catalytic composite per hour.

For the oligomerization of isobutene, however, it is more advantageous to feed above the catalytic zone (Table 9).

TABLE 9

Feed position effect on isobutene oligomerization

|  | S1CD4 | S1CD9 |
|---|---|---|
| Reaction conditions: | | |
| Reaction pressure, psig | 60 | 60 |
| Reaction temperature, ° C. | 62-88 | 55-84 |
| Reboiler duty, W | 300 | 300 |
| Amount of catalytic composite, g | 75 | 75 |
| Nickel concentration, wt % | 1.5 | 1.5 |
| Catalyst position, ft | 10.7-12.7 | 10.7-12.7 |
| Feed rate of isobutene, g/h | 58.30 | 58.30 |
| Feed rate of isopentane, g/h | 63.25 | 63.25 |
| Feed position | Below | Above |
| Results: | | |
| Conversion, wt % | 93.45 | 91.47 |
| Selectivity, wt % | 68.82 | 74.97 |
| Productivity, g/g · h | 0.73 | 0.71 |
| C8 productivity, g/g · h | 0.50 | 0.53 |

Selectivity represents the weight fraction of octenes out of total oligomers.
Productivity represents the weight of oligomers produced by unit weight of catalytic composite per hour.

Example 8

Comparison of CD and Batch Reactors.
Oligomerization of 1-Butene and Isobutene

The advantages of a CD reactor for the dimerization of isobutene can be seen in Table 10.

TABLE 10

A comparison of the catalytic composite performance among the different types of reactors for 1-butene oligomerization

|  | Batch reactor | Flow reactor | CD reactor |
|---|---|---|---|
| Reaction conditions: | | | |
| Reaction temperature, ° C. | 110 | 110 | 101-122 |
| 1-butene flow rate (g/h) or its amount (g) | 40 | 13.37 | 66.37 |
| Catalyst, g | 3.0 | 10 | 79.45 |
| Catalytic composite type | Ni/γ alumina | Ni/γ alumina | Ni/γ alumina |
| Ni concentration, wt % | 3.0 | 3.0 | 3.0 |
| Catalyst size, mm | 15 | 2.0 | 15 |
| Reaction time or residence time (min) | 60 | 44.88 | 71.82 |
| Results: | | | |
| Conversion, wt % | 29.83 | 71.61 | 88.03 |
| Selectivity, wt % | 78.91 | 64.81 | 87.51 |
| Productivity, g/g · h | 3.98 | 1.15 | 0.74 |

Residence time represents the weight of catalytic composite/mass flow rate of 1-butene.
Selectivity represents the weight fraction of octenes out of total oligomers.
Productivity represents the weight of oligomers produced by unit weight of catalytic composite per hour.

Under similar reaction conditions such as temperature and reaction time, the conversion and selectivity of the oligomerization reaction carried out in a CD column is much higher than a batch reactor or a flow reactor. This shows that the catalytic composite containing Ni under CD conditions gives a high conversion and selectivity to the octene dimer compared to a batch or flow reactor system.

Example 9

Other Catalytic Active Species for Oligomerization of Lower Alkenes

Besides $NiSO_4$ as a catalytic component on a porous support such as γ alumina, other catalytic material such as $(NH_4)Fe(SO_4)_2$, $FeSO_4$ and $(NH_4)_2SO_4$ are also active for the dimerization and oligomerization of isobutene (Table 11).

TABLE 11

Effect of different metal sulfates for isobutene oligomerization

| Reaction conditions: | | | | | |
|---|---|---|---|---|---|
| Reaction temperature, ° C. | 65 | 65 | 65 | 65 | 65 |
| Amount of Isobutene, g | 45 | 45 | 45 | 45 | 45 |
| Amount of catalyst, g | 3 | 3 | 3 | 3 | 3 |

TABLE 11-continued

Effect of different metal sulfates for isobutene oligomerization

| Catalytic phase | $(NH_4)_2Fe(SO_4)_2$ | $FeSO_4$ | $(NH_4)_2SO_4$ | $NiSO_4$ | $NiSO_4$ |
|---|---|---|---|---|---|
| Support | $\gamma\text{-}Al_2O_3$ | $\gamma\text{-}Al_2O_3$ | $\gamma\text{-}Al_2O_3$ | $\gamma\text{-}Al_2O_3$ | $\gamma\text{-}Al_2O_3$ |
| Ni concentration, wt % | 0 | 0 | 0 | 1.5 | 3.0 |
| $SO_4^{2-}$ concentration, wt % | 10.3 | 5.2 | 4.9 | 2.5 | 4.9 |
| Reaction time, min | 75 | 60 | 60 | 60 | 60 |
| Results: | | | | | |
| Conversion, wt % | 3.7 | 50.6 | 33.9 | 14.20 | 53.1 |
| Selectivity, wt % | 61.6 | 17.3 | 46.3 | 38.0 | 25.0 |

Selectivity represents the weight fraction of octenes out of total oligomers.

Example 10

Effect of Ni Salts on the Oligomerization of 1-Butene

Table 12 shows the activity of different Ni compounds on a porous support structure, based on γ alumina, for the oligomerization of 1-butene. Ni sulphate is more active than Ni chloride. Addition of $NH_4Cl$ to $NiCl_2$ increased the activity of $NiCl_2$. The surface area of the fresh and used catalyst are not very different indicating that the catalytic composites are quite stable. Table 13 shows that for the 1-butene oligomerization, the porous γ alumina is much more stable than the NaY zeolite or BaNaY zeolite used to support the $NiSO_4$ or $NiCl_2$ as can be seen from the reduction of the surface area of the used catalyst.

TABLE 12

A comparison of catalytic composite performance prepared by different catalytic phases supported on the porous γ alumina in the batch reactor

| Catalyst | Support | Nickel loading (wt %) | Reaction conditions | Conversion (wt %) | Selectivity (wt %) | Surface area $m^2/g$ |
|---|---|---|---|---|---|---|
| $NiCl_2$ | $\gamma Al_2O_3$ | 5.53 | 110° C., 600 psi, 2 hrs | 12.53 | 93.28 | Fresh = 183.2 Used = 188.5 |
| $NiCl_2 + NH_4Cl$ | $\gamma Al_2O_3$ | 5.53 | 110° C., 600 psi, 2 hrs | 28.85 | 87.89 | Fresh = 185.7 Used = 190.1 |
| $NiSO_4$ | $\gamma Al_2O_3$ | 4.04 | 110° C., 600 psi, 2 hrs | 36.71 | 72.15 | Fresh = 186.5 Used = 187.0 |
| $NiSO_4$ | $\gamma Al_2O_3$ | 4.04 | 60° C., 600 psi, 2 hrs | 19.15 | 77.35 | Fresh = 186.5 Used = 188.3 |
| NiMo | $\gamma Al_2O_3$ | >10 | 110° C., 600 psi, 2 hrs | 19.85 | 38.11 | Fresh = 148.1 Used = 144.1 |

Selectivity represents the weight fraction of octenes out of total oligomers

TABLE 13

A comparison of catalyst performance prepared using different supports in a batch reactor

| Catalytic Phase | Support | Nickel loading (wt %) | Reaction conditions | Conversion (wt %) | Selectivity (wt %) | Surface area $m^2/g$ |
|---|---|---|---|---|---|---|
| $NiCl_2$ | $\gamma Al_2O_3$ | 5.53 | 110° C., 600 psi, 2 hrs | 12.53 | 93.28 | Fresh = 183.2 Used = 188.5 |
| $NiCl_2$ | NaY | 4.85 | 110° C., 600 psi, 2 hrs | 52.15 | 69.51 | Fresh = 622.9 Used = 182.4 |

TABLE 13-continued

A comparison of catalyst performance prepared using different supports in a batch reactor

| Catalytic Phase | Support | Nickel loading (wt %) | Reaction conditions | Conversion (wt %) | Selectivity (wt %) | Surface area m²/g |
|---|---|---|---|---|---|---|
| NiCl₂ | BaNaY | 0.87 | 110° C., 600 psi, 2 hrs | 39.18 | 81.58 | Fresh = 581.5 Used = 363.2 |
| NiSO₄ | Al₂O₃ | 4.04 | 110° C., 600 psi, 2 hrs | 36.71 | 72.15 | Fresh = 186.5 Used = 187.0 |
| NiSO₄ | NaY | 5.20 | 110° C., 600 psi, 2 hrs | 41.82 | 73.26 | Fresh = 635.8 Used = 211.9 |

Selectivity represents the weight fraction of octenes out of total oligomers.

Example 11

One Step Production of Isooctane from Isobutene Oligomerization and Hydrogenation in a CD Column This example shows that high selectivity for the one step production of isooctane from isobutene can be achieved using a process where two separate catalytic distillation zones are used in the same distillation column, the upper catalyst zone containing a dimerization/oligomerization catalyst and a lower catalyst zone containing a hydrogenation catalytic composite. In the dimerization zone, a Ni catalytic composite was mixed with an approximately equal volume of intalox saddles. The isobutene can be fed anywhere above or immediately below the dimerization zone. The hydrogen should be fed below the hydrogenation zone. In the dimerization zone, the catalytic composite contained 1 wt % nickel. In the hydrogenation zone, the catalytic composite contained 0.7 wt % Pd. Table 14 shows the results of the one step reaction. When no hydrogen was fed into the column (see Run number 2-3), the oligomers consisted of 84.9 wt % octenes, 13.5 wt % dodecenes and 1.6 wt % hexadecenes, and the selectivity to octenes was 84.9 wt %. The octenes consisted of 77.8 wt % 2,4,4 trimethylpentene-1 and 22.2 wt % of 2,4,4 trimethylpentene-2. When hydrogen was introduced into the catalytic distillation column below the reaction zone containing the Pd catalytic composite (Run number 2-2), over 98% hydrogenation of the octenes to 2,2,4-trimethylpentane (octane rating of 100) was achieved. Some hydrogenation of dodecenes and hexadecenes also occurred. The presence of hydrogen did not reduce the productivity for the dimerization of isobutene to octenes and a slight increase in oligomerization was observed in the given experiment. The hydrogen flow rate should be controlled such that the amount of hydrogen fed is sufficient to hydrogenate the oligomers. Lowering of the reboiler duty from 350 W to 300 W did not significantly affect the productivity of octenes or the production of 2,2,4 trimethylpentane (Comparing Run number 2-5 and Run number 2-2). Comparison of Run number 2-5 and Run number 2-8 in Table 14 shows that increasing the isobutene feed rate increased the oligomerization activity and also the productivity of 2,2,4 trimethylpentane.

Since the pressure in the column controls the temperature in a catalytic distillation column, the pressure in the column should be such that the temperature profile in the CD column is suitable for producing the oligomers at the top section of the CD column and the hydrogenation occurs at the bottom section of the CD column. An example of the effect of pressure on the process is shown in Table 15. It can be seen that on increasing the pressure, the temperatures in the oligomerization zone and the hydrogenation zone increased, the oligomerization activity and the productivity of 2,2,4-trimethylpentane increased but the selectivity to octenes decreased.

The activities of the catalytic composites for dimerization/oligomerization and hydrogenation were stable over 20 days on stream.

TABLE 14

Effect of process parameters on production of 2,2,4 trimethylpentane from the oligomerization of isobutene and hydrogenation

| | Run number | | | |
|---|---|---|---|---|
| | 2-3 — | 2-5 H₂ | 2-2 H₂ | 2-8 H₂ |
| Reaction conditions: | | | | |
| Temperature at Ni catalytic composite zone | 75° C. | 75° C. | 75° C. | 75° C. |
| Temperature at Pd catalytic composite zone | 121° C. | 121° C. | 121° C. | 121° C. |
| Reboiler duty, W | 350 | 300 | 350 | 300 |
| Amount of Ni catalytic composite, g | 81.5 | 81.5 | 81.5 | 81.5 |
| Amount of Pd catalytic composite, g | 224.6 | 224.6 | 224.6 | 224.6 |
| Ni catalytic composite position from reboiler, distance in feet | 11.5-13.5 | 11.5-13.5 | 11.5-13.5 | 11.5-13.5 |
| Pd catalytic composite position from reboiler, distance in feet | 0.3-4.3 | 0.3-4.3 | 0.3-4.3 | 0.3-4.3 |
| Feed rate of isobutene, g/h | 49.95 | 49.95 | 49.95 | 62.85 |
| Feed rate of isopentane, g/h | 69.74 | 69.74 | 69.74 | 44.64 |
| H₂ feed rate (L/hr @ STP) | — | 8.77 | 8.77 | 13.21 |
| Results: | | | | |
| Oligomerization activity, g/g · h | 0.51 | 0.51 | 0.54 | 0.85 |
| Selectivity to octenes, wt % | 84.9 | 86.37 | 87.32 | 84.37 |
| Productivity of 2,2,4-trimethylpentane, g/g · h | — | 0.16 | 0.17 | 0.25 |

Selectivity represents the weight fraction of octenes out of total oligomers.
Oligomerization activity represents the weight of octenes, dodecenes and hexadecenes produced by unit weight of catalyst per hour.

TABLE 15

Effect of pressure on production of isooctane from the oligomerization of isobutene and hydrogenation

| | Run number | | |
|---|---|---|---|
| | 4-17 $H_2$ | 4-15 $H_2$ | 4-18 $H_2$ |
| Reaction conditions: | | | |
| Temperature at Ni catalytic composite zone | 76° C. | 78° C. | 85° C. |
| Temperature at Pd catalytic composite zone | 124° C. | 125° C. | 130° C. |
| Pressure, psig | 100 | 125 | 150 |
| Amount of Ni catalytic composite, g | 81.5 | 81.5 | 81.5 |
| Amount of Pd catalytic composite, g | 224.6 | 224.6 | 224.6 |
| Ni catalytic composite position from reboiler, distance in feet | 11.5-13.5 | 11.5-13.5 | 11.5-13.5 |
| Pd catalytic composite position from reboiler, distance in feet | 0.3-4.3 | 0.3-4.3 | 0.3-4.3 |
| Feed rate of isobutene, g/h | 68.37 | 68.37 | 79.83 |
| Feed rate of isopentane, g/h | 78.46 | 78.46 | 66.83 |
| $H_2$ feed rate(L/hr @ STP) | 8.77 | 8.77 | 15.01 |
| Results: | | | |
| Oligomerization activity, g/g · h | 0.79 | 0.83 | 0.92 |
| Selectivity to octenes, wt % | 85.24 | 83.07 | 58.73 |
| Productivity of 2,2,4-trimethylpentane, g/g · h | 0.20 | 0.20 | 0.28 |

Selectivity represents the weight fraction of octenes out of total oligomers. Oligomerization activity represents the weight of octenes, dodecenes and hexadecenes produced by unit weight of catalyst per hour.

Example 12

Hydrogenation of Butadiene 3.7 g of Pd acetylacetonate was dissolved in 100 g of dichloromethane, and the solution obtained was added to 50 g of α-alumina rings of diameter and length of 8 mm (surface area 0.22 m$^2$/g) which were dried at 200° C. The solution containing the α-alumina rings was shaken at room temperature for 24 hours. The α-alumina rings containing Pd were taken out from the solution and dried in oven at 90° C. for 24 hours. Calcination was carried out at 350° C. for 3 hours, followed by reduction with hydrogen at 350° C. for 3 hours. The catalytic composite was protected from air. The weight of Pd in the catalytic composite was 0.31 wt %.

Hydrogenation of butadiene in a mixture of butadiene and isobutene was carried out in a batch autoclave using the above catalytic composite. Selective hydrogenation of butadiene to 1-butene and 2-butenes and n-butane was obtained between temperatures of 50-90° C. and pressures of 160-300 psig in a batch autoclave, for a mixture containing 5.4 wt % butadiene in isobutene. The catalytic composite weight was between 1.63 to 2.45 g with Pd loading of 0.31 wt %. In about 2-4 hours, 100% hydrogenation of butadiene was obtained.

All publications, patents and patent applications cited in this specification are herein incorporated by reference as if each individual publication, patent or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a", "an", and "the" include plural reference unless the context clearly dictates otherwise. Unless defined otherwise all technical and scientific terms used herein have the same meaning as commonly understood to one of ordinary skill in the art to which this invention belongs.

We claim:

1. A process for the selective dimerization of a lower alkene to a $C_6$-$C_{12}$ alkene, which process comprises contacting, under catalytic distillation conditions, the lower alkene with a catalytic composite comprising:
   a) a support structure, made of a non zeolite inorganic oxide, having a void fraction ranging from 0.30 to 0.95 and a surface area of from 40 m$^2$/g to 500 m$^2$/g, the support structure having a shape selected from a ring, a hollow cylinder, a cross or multi partition ring or cylinder with 2, 3, or 4 cell partitions, a saddle, a solid ring, a solid cylinder, a sphere, and a honeycomb body; and
   b) from 0.01 to 10% by weight of a catalytically active species comprising a group VIII metal, based on the weight of the catalytic composite, which is deposited on the support structure.

2. The process according to claim 1, wherein the lower alkene is selected from 1-butene, 2-butene and isobutene, and the $C_6$-$C_{12}$ alkene is selected from trimethylpentene, n-octene, dimethylhexene and methylheptene.

3. The process according to claim 1, wherein the catalytic composite is admixed with inert distillation packing.

4. The process according to claim 3, wherein the ratio of the catalytic composite to inert distillation packing is from 10:1 to 1:10.

5. The process according to claim 3, wherein the catalytic composite and inert distillation packing are used in separate zones of the catalytic distillation column.

6. The process according to claim 1, wherein the lower alkene is a $C_4$ alkene and the $C_6$ to $C_{12}$ alkene is predominantly a $C_8$ alkene.

7. The process according to claim 6, wherein the $C_8$ alkene is a trimethylpentene.

8. A process for preparing high octane compounds, the process comprising:
   a) contacting, under catalytic distillation conditions to obtain a $C_6$ to $C_{18}$ alkene, a $C_2$ to $C_6$ alkene with a first catalytic composite, the first catalytic composite comprising:
      (i) a support structure, made of a non zeolite inorganic oxide, having a void fraction ranging from 0.30 to 0.95 and a surface area of from 40 m$^2$/g to 500 m$^2$/g, the support structure having a shape selected from a ring, a hollow cylinder, a cross or multi partition ring or cylinder with 2, 3, or 4 cell partitions, a saddle, a solid ring, a solid cylinder, a sphere, and a honeycomb body, and
      (ii) from 0.01 to 10% by weight of a catalytically active species comprising a group VIII metal, based on the weight of the catalytic composite, which is deposited on the support structure; and
   b) contacting, under catalytic distillation conditions to obtain a $C_6$ to $C_{18}$ alkane, the $C_6$ to $C_{18}$ alkene from step a) with a second catalytic composite and hydrogen, the second catalytic composite comprising:

(i) a support structure, made of a non zeolite inorganic oxide, having a void fraction ranging from 0.30 to 0.95 and a surface area of from 40 m²/g to 500 m²/g, the support structure having a shape selected from a ring, a hollow cylinder, a cross or multi partition ring or cylinder with 2, 3, or 4 cell partitions, a saddle, a solid ring, a solid cylinder, a sphere, and a honeycomb body, and (ii) from 0.01 to 10% by weight of a catalytically active species comprising a group VIII metal, based on the weight of the catalytic composite, which is deposited on the support structure, and a ligand comprising one or more atoms selected from the group consisting of carbon, hydrogen, oxygen, nitrogen and phosphorus.

9. The process according to claim 8, wherein the process steps a) and b) are carried out in a single catalytic distillation column.

10. The process according to claim 8, wherein the process steps a) and b) are carried out in separate catalytic distillation columns.

11. The process according to claim 8, wherein the $C_2$ to $C_6$ alkene is a $C_4$ alkene and the $C_6$ to $C_{18}$ alkene is a $C_8$ alkene.

12. The process according to claim 11, wherein the $C_8$ alkene is trimethylpentene.

13. A process for the production of $C_6$-$C_8$ alkenes, which process comprises contacting, under catalytic distillation conditions, a mixture of $C_2$-$C_6$ alkenes with a catalytic composite comprising:

a) a support structure, made of a non zeolite inorganic oxide, having a void fraction ranging from 0.30 to 0.95 and a surface area of from 40 m²/g to 500 m²/g, the support structure having a shape selected from a ring, a hollow cylinder, a cross or multi partition ring or cylinder with 2, 3, or 4 cell partitions, a saddle, a solid ring, a solid cylinder, a sphere, and a honeycomb body; and b) from 0.01 to 10% by weight of a catalytically active species comprising a group VIII metal, based on the weight of the catalytic composite, which is deposited on the support structure.

14. A process according to claim 13, wherein each $C_2$-$C_6$ alkene in the mixture is oligomerized within different reactive zones found in a single catalytic distillation column.

15. A process according to claim 13, wherein each $C_2$-$C_6$ alkene is oligomerized within different reactive zones found in two or more linked catalytic distillation column.

16. A process according to claim 13, wherein the mixture of $C_2$-$C_6$ alkenes comprises one or more $C_4$ alkenes.

17. A process for the selective oligomerization of a lower alkene to a $C_6$-$C_{18}$ alkene, which process comprises contacting, under catalytic distillation conditions, a mixture of $C_2$ to $C_6$ alkenes and $C_1$ to $C_6$ alkanes with a catalytic composite comprising:

a) a support structure, made of a non zeolite inorganic oxide, having a void fraction ranging from 0.30 to 0.95 and a surface area of from 40 m²/g to 500 m²/g, the support structure having a shape selected from a ring, a hollow cylinder, a cross or multi partition ring or cylinder with 2, 3, or 4 cell partitions, a saddle, a solid ring, a solid cylinder, a sphere, and a honeycomb body; and b) from 0.01 to 10% by weight of a catalytically active species comprising a group VIII metal, based on the weight of the catalytic composite, which is deposited on the support structure.

18. The process according to claim 1, wherein the inorganic oxide is selected from the group consisting of alumina, silica, titania, zirconia and mixtures thereof, preferably from γ-alumina and α-alumina.

19. The process according to claim 1, wherein the support structure is in the shape of a Raschig ring.

20. The process according to claim 1, wherein the group VIII metal is nickel.

21. The process according to claim 1, wherein the group VIII metal is in the form of a metal salt, preferably a metal sulphate, a metal phosphate, a metal oxalate or a metal acetate, or in the form of a metal complex.

22. The process according to claim 1, wherein the catalytically active species is nickel sulphate or nickel chloride.

23. The process according to claim 21, wherein the metal salt is in an ionic state and the catalytically active species is in admixture with ammonium sulphate or ammonium phosphate.

24. The process according to claim 1, wherein the catalytically active species comprises a group VIII metal and a ligand, wherein the ligand comprises one or more atoms selected from the group consisting of carbon, hydrogen, oxygen, nitrogen and phosphorus.

25. The process according to claim 8, wherein the inorganic oxide is selected from the group consisting of alumina, silica, titania, zirconia and mixtures thereof, preferably from γ-alumina and α-alumina.

26. The process according to claim 8, wherein the support structure is in the shape of a Raschig ring.

27. The process according to claim 8, wherein the group VIII metal in the first catalytic composite is nickel.

28. The process according to claim 8, wherein the group VIII metal in the first catalytic composite is in the form of a metal salt, preferably a metal sulphate, a metal phosphate, a metal oxalate or a metal acetate, or in the form of a metal complex.

29. The process according to claim 8, wherein the catalytically active species in the first catalytic composite is nickel sulphate or nickel chloride.

30. The process according to claim 28, wherein the metal salt is in an ionic state and the catalytically active species is in admixture with ammonium sulphate or ammonium phosphate.

31. The process according to claim 8, wherein the catalytically active species in the first catalytic composite comprises a group VIII metal and a ligand, wherein the ligand comprises one or more atoms selected from the group consisting of carbon, hydrogen, oxygen, nitrogen and phosphorus.

32. The process according to claim 13, wherein the inorganic oxide is selected from the group consisting of alumina, silica, titania, zirconia and mixtures thereof, preferably from γ-alumina and α-alumina.

33. The process according to claim 13, wherein the support structure is in the shape of a Raschig ring.

34. The process according to claim 13, wherein the group VIII metal is nickel.

35. The process according to claim 13, wherein the group VIII metal is in the form of a metal salt, preferably a metal sulphate, a metal phosphate, a metal oxalate or a metal acetate, or in the form of a metal complex.

36. The process according to claim 13, wherein the catalytically active species is nickel sulphate or nickel chloride.

37. The process according to claim 35, wherein the metal salt is in an ionic state and the catalytically active species is in admixture with ammonium sulphate or ammonium phosphate.

38. The process according to claim 13, wherein the catalytically active species comprises a group VIII metal and a ligand, wherein the ligand comprises one or more atoms selected from the group consisting of carbon, hydrogen, oxygen, nitrogen and phosphorus.

39. The process according to claim 17, wherein the inorganic oxide is selected from the group consisting of alumina, silica, titania, zirconia and mixtures thereof, preferably from γ-alumina and α-alumina.

40. The process according to claim 17, wherein the support structure is in the shape of a Raschig ring.

41. The process according to claim 17, wherein the group VIII metal is nickel.

42. The process according to claim 17, wherein the group VIII metal is in the form of a metal salt, preferably a metal sulphate, a metal phosphate, a metal oxalate or a metal acetate, or in the form of a metal complex.

43. The process according to claim 17, wherein the catalytically active species is nickel sulphate or nickel chloride.

44. The process according to claim 17, wherein the metal salt is in an ionic state and the catalytically active species is in admixture with ammonium sulphate or ammonium phosphate.

45. The process according to claim 17, wherein the catalytically active species comprises a group VIII metal and a ligand, wherein the ligand comprises one or more atoms selected from the group consisting of carbon, hydrogen, oxygen, nitrogen and phosphorus.

46. The process according to claim 8, wherein the group VIII metal in the second catalytic composite comprises a Group VIII metal which is in the zero oxidation state.

47. The process according to claim 8, wherein the Group VIII metal in the second catalytic composite comprises palladium, platinum or rhodium.

* * * * *

UNITED STATES PATENT AND TRADEMARK OFFICE
CERTIFICATE OF CORRECTION

PATENT NO. : 7,718,569 B2
APPLICATION NO. : 10/582333
DATED : May 18, 2010
INVENTOR(S) : Flora Tak Tak Ng et al.

It is certified that error appears in the above-identified patent and that said Letters Patent is hereby corrected as shown below:

Column 1, line 31: "(Backhaus, 1921)" should be --(Backhaus, US Patent No. 1,400,849)--

Column 1, lines 35 & 36: "(Smith, 1980)." should be --(Smith, US Patent No. 4,232,177).--

Column 2, line 11: "Smith (1980)" should be --Smith (US Patent No. 4,232,177)--

Column 3, line 19: "(1990) and Smith et al. (1991)." should be --(US Patent No. 4,935,577 and Smith et al. US Patent No. 5,003,124).--

Column 3, lines 48 & 49: "(Keim et al., 1979; Mathys, 1984; Beltrame et al., 1994)" should be --(Keim et al., J. Mol. Catal., 6, 79, 1979; Mathys et al., US Patent No. 4,476,341; and Beltrame et al., Appl. Catal., A: general, 100, 39-48,1994)--

Column 3, line 64: "Podrebarac (1992)" should be --Podrebarac ("The Dimerization of 1-Butene Using Catalytic Distillation", M.A. Sc. Thesis, University of Waterloo, 1992)--

Column 4, line 54: "which is deposited on the support structure," should be --which is deposited on the support structure. In one embodiment, the inorganic oxide forming the support structure of the hydrogenation catalyst is an α-alumina, for example an α-alumina having a surface area of from 0.1 to 1.0 m2/g.--

Column 7, line 59: "species for oligomerization. More preferably, the nickel ions" should be --species for oligomerization. Examples of metal salts include metal sulphate, metal phosphate, metal oxalate and metal acetate. More preferably, the nickel ions--

Column 8, line14: "by the nickel catalyst described herein. Metal salts can also be" should be --by the nickel catalyst described herein. Metal complexes can contain ligands comprising, for example, one or more carbon, hydrogen, oxygen, nitrogen and phosphorus atoms. Metal salts can also be--

Signed and Sealed this
First Day of February, 2011

David J. Kappos
*Director of the United States Patent and Trademark Office*

CERTIFICATE OF CORRECTION (continued)
U.S. Pat. No. 7,718,569 B2

Column 27, claim 13, line 25: "A process for the production of C6-C8 alkenes, which" should be --A process for the production of C6-C18 alkenes, which--